United States Patent [19]

Hendrickson

[11] Patent Number: 5,404,292
[45] Date of Patent: Apr. 4, 1995

[54] DATA PROCESSING SYSTEM AND METHOD FOR AUTOMATICALLY PERFORMING PRIORITIZED NURSING DIAGNOSES FROM PATIENT ASSESSMENT DATA

[75] Inventor: Maria F. Hendrickson, Chemlsford, Mass.

[73] Assignee: Hewlett-Packard Company, Palo Alto, Calif.

[21] Appl. No.: 227,292

[22] Filed: Apr. 13, 1994

Related U.S. Application Data

[63] Continuation of Ser. No. 757,856, Sep. 11, 1991, abandoned.

[51] Int. Cl.$^6$ ............................................. G06F 15/42
[52] U.S. Cl. ................................................ 364/413.02
[58] Field of Search ..................... 364/413.02, 413.01, 364/413.03, 413.05, 413.06, 413.08, 413.09, 413.11; 395/50, 51, 52, 54, 60, 61, 76

[56] References Cited

U.S. PATENT DOCUMENTS

| | | |
|---|---|---|
| 4,290,114 | 9/1981 | Sinay . |
| 4,649,515 | 3/1987 | Thompson et al. . |
| 4,730,259 | 3/1988 | Gallant . |
| 4,733,354 | 3/1988 | Potter et al. . |
| 4,839,822 | 6/1989 | Dormond et al. . |
| 4,967,368 | 10/1990 | Bolling et al. .................... 395/61 |
| 4,975,840 | 12/1990 | Detore et al. .................... 364/401 |
| 5,063,522 | 11/1991 | Winters ............................ 395/51 |
| 5,133,046 | 7/1992 | Kaplan ............................. 395/61 |

FOREIGN PATENT DOCUMENTS 0457000  11/1991  European Pat. Off. .

OTHER PUBLICATIONS

"Extending the Feature Dictionary to Support Sophisticated Feature Interaction and Classification", Samuels et al., Proceedings Second Annual IEEE Symposium on Computer-Based Medical Systems, Jun. 26-27, 1989 pp. 29-35.

"Computers in Cardiology", Sep. 25-28, 1988 pp. 185-188, Paper on Differential Diagnosis Generation From a Causal Network with Probabilities.
IEEE Transactions on Bio-Medical Engineering.
IEEE Expert.
Proceedings of Computers in Cardiology, IEEE Computer Society Press.
Proceedings of the Second Annual Symposium on Computer-Based Medical System.
ICL Technical Journal.

(List continued on next page.)

*Primary Examiner*—Donald E. McElheny, Jr.

[57] ABSTRACT

A data processing system and method for automatically performing prioritized nursing diagnoses from patient assessment data stores a diagnosis table containing relations between nursing diagnoses and patient characteristics, with each such relation having a corresponding probability measure. A priority table containing at least one relation between a diagnosis from a diagnosis table and a corresponding priority measure is also stored. The data processing system receives assessment data, matches assessment data with relations in the diagnosis table and constructs a potential diagnosis list including the matched diagnoses and the corresponding probability measures. The probability measure of each diagnosis in the potential diagnosis list is weighted with the priority measure corresponding to the diagnosis from the priority table. When more than one relation is provided for a diagnosis in the diagnosis table, probability measures are combined when the potential diagnosis list is constructed. The probability measures are preferably added together to combine them, and are preferably limited to a maximum value, for example, equivalent to 99%. The diagnosis table may be divided into primary and secondary diagnoses tables. Each relation in the primary diagnosis table has the same probability measure. The tables and lists of the data processing system and method preferably implemented in a relational database.

18 Claims, 10 Drawing Sheets

OTHER PUBLICATIONS

Abraham, I. and Schultz, S. "Knowledge Representation in Clinical Inference in Nursing: Structures and Their Application to Information Systems," Medinfo 1986, (North Holland: Elsevier Science Publishers, 1986), pp. 194–198.

Aikins, J. et al. "PUFF: An Expert System for Interpretation of Pulmonary Function Data." Readings In Medical Artificial Intelligence, The First Decade, Clancey, W. and Shortliffe, E. eds. (Reading, Mass.: Addison-Wesley Publ. Co., 1984), pp. 444–445.

Benner, P. and Tanner, C. "Clinical Judgment: How Expert Nurses Use Intuition." Decision Support Systems in Nursing, Ozbolt, J., Vandewal, D. and Hannah, K., eds. (St. Louis: The C. V. Mosby Company, 1990), pp. 193–205.

Brennan, P. "Computerized Decision Support: Beyond Expert Systems," Decision Support Systems in Nursing, Ozbolt, J., Vandewal, D. and Hannah, K., eds. (St. Louis: The C. V. Mosby Company, 1990), pp. 165–170.

Brennan, P. "Decision Support Systems in Nursing: An Overview." Decision Support Systems in Nursing, Ozbolt, J., Vandewal, D. and Hannah, K., etc. (St. Louis: The C. V. Mosby Company, 1990) pp. 3–14.

Brennan, P. "Home Care Nursing Via Computer Networks," Decision Support Systems in Nursing, Ozbolt, J., Vandewal, D. and Hannah, K., eds. (St. Louis: The C. V. Mosby Company, 1990), pp. 171–180.

Brennan, P. "Modeling for Decision Support." Nursing Informatics: Where Caring and Technology Meet, Ball, M. et al eds., (New York: Springer-Verlag, 1988), pp. 267–273.

Carnevali, D. "The Diagnostic Reasoning Process." Diagnostic Reasoning in Nursing, Carnevali et al, eds. (New York: J. B. Lippincott, 1984) pp. 25–28.

Chang, B. et al., "Candi-A Knowledge-based System for Nursing Diagnosis." Computers in Nursing, vol. 6, No. 1, 1988, pp. 13–21.

Chase, S. "Knowledge Representation in Expert Systems-Nursing Diagnosis Applications." Computers in Nursing, vol. 6, No. 2, pp. 58–64, 1988.

Clancey, W. and Letsinger, R. "NEOMYCIN: Reconfiguring a Rule-Based Expert System for Application to Teaching." Readings in Medical Artificial Intelligence, The First Decade, Clancy, W. and Shortliffe, E., eds. (Reading, Mass.: Addison-Wesley Publishing Company, 1984), pp. 361–181.

Evans, S. "Challenges Facing the Distribution of an Artificial Intelligence Based System for Nursing." Journal of Medical Systems, vol. 9, Nos. $\frac{1}{2}$, 1985, pp. 79–89.

Evans, S. "The Commes Nursing Consultant System." Decision Support Systems in Nursing, Ozbolt, J., Vandewal, D. and Hannah, K., eds. (St. Louis: The C. V. Mosby Company, 1990), pp. 97–120.

Evans, S. "A Computer-Based Nursing Diagnosis Consultant." Proceedings Eight Annual Symposium on Computer Applications in Medical Care, (Silver Spring: The IEEE Computer Society Press, 1984), pp. 658–661.

Fagan, L. et al. "Computer-Based Medical Decision Making: From MYCIN to VM." Readings in Medical Artificial Intelligence, The First Decade, Clancey, W. and Shortliffe, E., eds. (Reading, Mass.: Addison-Wesley Publishing Co., 1984), pp. 241–255.

Hannah, K. "Classification of Decision Support Systems." Nursing Informatics: Where Caring and Technology Meet, Ball, M. et al., eds., (New York: Springer-Verlag, 1988), pp. 261–266.

Hannah, K. "Understanding the Concepts of Computer Based Decision Support Systems for Nursing Practice," Clinical Judgment and Decision Making: The Future of Nursing Diagnoses, Hannah, K., Reimer, M., Mills, W. and Letourneau, L. eds., (New York: John Wiley and Sons, 1987), pp. 513–519.

Heriot, C. et al. "A Pain Management Decision Support System for Nurses." Decision Support Systems in Nursing, Ozbolt, J., Vandewal, D. and Hannah, K., eds. (St. Louis: The C. V. Mosby Company, 1990), pp. 153–164.

Hillis, T. and S. Evans. "Commes-A Nursing AI-Based Expert System." Medinfo 86, (North Holland: Elsevier Science Publishers, 1986), p. 1140.

Hovenga, E. et al. "Decision Support Systems in Nursing Practice: A Look to the Future." Decision Support Systems in Nursing, Ozbolt, J., Vandewal, D. and Hannah, K., eds. (St. Louis: The C. V. Mosby Company), 1990, pp. 15–27.

Jones, B. "Building Nursing Expert Systems Using Automated Rule Induction". Computers in Nursing, vol. 9, No. 2, 1991, pp. 52–60.

Miller, R. et al. "INTERNIST-A, An Experimental Computer-Based Diagnostic Consultant for General Internal Medicine". Readings in Medical Artificial Intelligence, The First Decade, Clancey, W. and Shortliffe, E., eds. (Reading, Mass.: Addison-Wesley Publishing Co., 1984), pp. 190–209.

(List continued on next page.)

OTHER PUBLICATIONS

Ozbolt, J. G. "Developing Decision Support Systems for Nursing: Issues of Knowledge Representation." Medinfo 1986, (North Holland: Elsevier Sciece Publishers, 1986), pp. 186-189.

Ozbolt, J. G. "Knowledge-Based Systems for Supporting Clinical Nursing Decisions." Nursing Informatics: Where Caring and Technology Meet, Ball, M. et al eds., (New York: Springer-Verlag, 1988), pp. 274-285.

Ozbolt, J. "Prolog: A Practical Language for Decision Support Systems in Nursing?" Decision Support Systems in Nursing, Ozbolt, J., Vandewal, D. and Hannah, K., eds. (St. Louis: The C. V. Mosby Company, 1990), pp. 129-138.

Ozbolt, J., Schultz, S., Swain, M., Abraham, I. and Farchaus-Stein, K. "Developing an Expert System for Nursing Practice." Eighth Annual Symposium on Computer Applications in Medical Care, (Silver Spring: The IEEE Computer Society Press, 1984), pp. 654-657.

Ozbolt, J., Schultz, S., Swain, M., & Abraham, I. "A Proposed Expert System for Nursing Practice." Journal of Medical Systems, vol. 9, Nos. ½, 1985, pp. 57-68.

Ozbolt, J. and Swain, M. "Representing a Nursing Knowledge Base for a Decision Support System in Prolog." Decision Support Systems in Nursing, Ozbolt, J., Vandewal, D. and Hannah, K., eds, (St. Louis: The C. V. Mosby Company, 1990), pp. 139-152.

Probst, C. and Rush, J. "The Careplan Knowledge Base: A Prototype Expert System for Postpartum Nursing Care." Computers in Nursing, vol. 8, No. 5, 1990, pp. 206-213.

Ryan, S. "An Expert System for Nursing Practice." Computers in Nursing, Mar./Apr., 1985, pp. 77-84.

Ryan, S. "An Expert System for Nursing Practice." Journal of Medical Systems, vol. 9, Nos. ½, 1985, pp. 29-41.

Shortliffe, E. "Knowledge Engineering for Medical Decision Making." Readings in Medical Artificial Intelligence, The First Decade, Clancey, W. and Shortliffe, E., eds. (Reading, Mass.: Addison-Wesley Publishing Co., 1984), pp. 36-71.

Shortliffe, E. and Clancy, W. "Anticipating the Second Decade." Readings in Medical Artificial Intelligence, The First Decade, Clancey, W. and Shortliffe, E., eds. (Reading, Mass.: Addison-Wesley Publishing Co., 1984), pp. 463-472.

Sinclair, Vaughn D. "Potential Effects of Decision Support Systems on the Role of the Nurse." Computers in Nursing, vol. 8, No. 2, 1990, pp. 60-65.

Tanner, C. et al. "Diagnostic Reasoning Strategies of Nurses and Nursing Students." Decision Support Systems in Nursing, Ozbolt, J., Vandewal, D. and Hannah, K., eds. (St. Louis: The C. V. Mosby Company, 1990), pp. 181-192.

Tanner, C. "Factors Influencing the Diagnostic Process." Diagnostic Reasoning in Nursing, Carnevali et al., eds. (New York: J. B. Lippicott, 1984), pp. 61-82.

Warnock-Matheron, A. and Hannah, K. "The Use of Expert Systems in Clinical Nursing Practice." Decision Support Systems in Nursing, Ozbolt, J., Vandewal, D. and Hannah, K., eds. (St. Louis: The C. V. Mosby Company, 1990), pp. 81-89.

Woods, N. "Methods for Studying Diagnostic Reasoning in Nursing." Diagnostic Reasoning in Nursing, Carnevali et al., eds. (New York: J. B. Lippicott, 1984), pp. 193-206.

Woolery, L. et al. "The Use of Machine Learning Program LERS-LB 2.5 in Knowledge Acquisition for Expert System Development in Nursing." Computers in Nursing, vol. 9, No. 6, 1991, pp. 227-234.

Wright, C. "Computer-Aided Nursing Diagnosis for Community Health Nurses." Nursing Clinics of North America, vol. 20, No. 3, Sep. 1985, pp. 487-495.

| | 74 | 76 | 78 |
|---|---|---|---|
| 72 | DIAGNOSIS | RAPID PULSE | 60% |

FIG. 4

| | 84 | 86 |
|---|---|---|
| 82 | DIAGNOSIS | 50 |

FIG. 5

| ADMIT ASSESSMT | 3 ICU WEST | WATSON, LULU | MRN #123-45678 | Dx: CAD | | ? |
|---|---|---|---|---|---|---|
| MAIN MENU | DATA ENTRY | OPTIONS | PRINT | | | HELP |

SELECT & CLICK ON CV ASSESSMENT ITEMS:

| | | | | | | |
|---|---|---|---|---|---|---|
| SKIN COLOR | WNL | PALE | CYANOTIC | GRAY | | |
| SKIN TEMP | WNL | DRY | COLD | DIAPHORETIC | | |
| APICAL PULSE | IRREG | BOUNDING | | | | |
| MURMUR | S1 | S2 | S3 | S4 | OTHER | |
| PERIPHERAL PULSE | WNL | ABN? | | | | |
| R FEMORAL | ABS | 1+ | 2+ | 3+ | | |
| L FEMORAL | ABS | 1+ | 2+ | 3+ | | |
| R POPLITEAL | ABS | 1+ | 2+ | 3+ | | |
| L POPLITEAL | ABS | 1+ | 2+ | 3+ | | |
| R DORSALIS | ABS | 1+ | 2+ | 3+ | | |
| L DORSALIS | ABS | 1+ | 2+ | 3+ | | |
| ANY RECENT EDEMA? | NO | YES | | | | |
| FAMILY hx OF CARDIAC DISEASE? | NO | YES | | | | |

HIGHLIGHT / CLEAR / CANCEL

- CV SYSTEM
- NEURO SYSTEM
- RESP SYSTEM
- MUSCULOSK SYSTEM
- GI SYSTEM
- GU SYSTEM
- INTEGU

SYSTEM MESSAGE AREA

THU 10 JUL 90 8:45 PM

FIG. 9

DATA PROCESSING SYSTEM AND METHOD FOR AUTOMATICALLY PERFORMING PRIORITIZED NURSING DIAGNOSES FROM PATIENT ASSESSMENT DATA

CROSS REFERENCE TO RELATED APPLICATION(S)

This is a continuation of application Ser. No. 07/757,856, filed on Sep. 11, 1991, now abandoned.

FIELD OF THE INVENTION

The present invention relates generally to data processing systems for performing diagnostic operations, more particularly to diagnostic systems related to health care, and more specifically to nursing diagnosis systems.

BACKGROUND OF THE INVENTION

An important aspect of nursing is the nursing process, a problem-solving approach applied to patient care. This nursing process includes four basic steps, which are assessment, planning, implementation and evaluation. Assessment involves the collection of signs and symptoms of a patient and the generation of prioritized nursing diagnoses by the nurse. Planning includes developing a plan of care to reach achievable outcomes for the patient based on the prioritized nursing diagnoses. The plan is then implemented for the patient, the outcomes are evaluated and the plan is revised.

Automation of the nursing process has been attempted in the past with concentration in the area of assessment and planning. Current automated systems, or expert systems, for generating nursing diagnoses fail to consider the method by which nurses actually make diagnoses. The diagnostic reasoning of nurses has been described by Carnevali, et al. in *Diagnostic Reasoning in Nursing* (New York: J. B. Lippincott, 1984) pages 25-28, 61-82, 193-206, which is hereby incorporated by reference. Carnevali et al. explain how nurses perform diagnoses based on assessment data, recognizing that there is some probabilistic relationship between the data and the diagnoses. However, the diagnostic reasoning process of nurses is also affected by a variety of biases which include the level of experience of the nurse, the amount of assessment data, stereotyping of patients, the frequency with which specific diagnoses and patient signs and symptoms occur, frequency of experience with specific signs and symptoms of the patient, and other experiences. Therefore, nurses may not always make correct diagnoses, and may fail to make important diagnoses. What Carnevali fails to note is that nurses often make multiple diagnoses which need to be prioritized in order to develop an adequate, prioritized care plan. The same biases which affected diagnoses also affect prioritization.

Another difficulty faced by nurses in performing diagnoses is that standard acceptable nursing diagnoses, generated by, for example, the North Atlantic Nursing Diagnoses Association (NANDA), are often insufficient to meet the needs of many specialized practice areas, and often change from year to year. Thus, nurses must continually keep up-to-date to know and use these nursing diagnoses. Current automated decision support systems, or expert systems, in nursing have failed to consider the constant change of acceptable nursing diagnoses. These previous systems include rules for making diagnoses which are "hard-coded" into the system. That is, when a system is implemented as a computer program in a computer language, such as LISP, the rules for diagnosis are also implemented in this computer language. Therefore, if any change needs to be made to the rules for diagnosis, a programmer needs to modify the system. Since acceptable nursing diagnoses change frequently, the maintenance of these systems becomes expensive, rendering them unsuitable for widespread use in hospitals. Moreover, nurses are not able to modify what they perceive to be the probabilistic relationship between signs and symptoms and diagnosis.

Finally, nurses often have experience in areas of specialty. Patients are grouped together according to these specialties into hospital care units, such as the intensive care unit, or the ambulatory care unit. In different care units, diagnoses have different likelihoods, different probabilistic relationships with patient data and different priorities. An inexperienced nurse often needs to rely on other experienced nurses to perform regular duties correctly.

In view of the problems and limitations of previous support systems for assisting nurses in performing diagnoses, it is an object of the present invention to provide a data processing system and method for automatically performing prioritized nursing diagnoses and which helps to reduce biases of a nurse.

Another object of the present invention is to provide a data processing system which permits nurses to transfer easily between specialized care units and to perform patient diagnoses while having little experience in a new care unit.

It is a further object of the present invention to provide a data processing system for automatically making nursing diagnoses from patient assessment data which recognizes the probabilistic relationship between patient data and diagnoses and prioritizes nursing diagnoses.

SUMMARY OF THE INVENTION

In view of the foregoing and other objects of the present invention, there is provided a data processing system and a method for automatically making prioritized nursing diagnoses. In one aspect of the invention, the data processing system stores a diagnosis table containing a relation between a nursing diagnosis and a patient characteristic, with each such relation having a corresponding probability measure. A priority table containing at least one relation between a diagnosis from the diagnosis table and a corresponding priority measure is also stored. The data processing system also receives assessment data, matches assessment data with relations in the diagnosis table and constructs a potential diagnosis list including the matched diagnoses and their corresponding probability measures. The probability measure of each diagnosis in the potential diagnosis list is weighted with the priority measure corresponding to the diagnosis from the priority table.

More than one relation may be provided for a diagnosis in the diagnosis table. In this case probability measures are combined in constructing the potential diagnosis list, to insure that a diagnosis appears once in the potential diagnosis list. In one embodiment, the probability measures are added together, and are preferably limited to a maximum value equivalent to 99%.

In another aspect of the invention there is provided a primary diagnosis table and a secondary diagnosis table.

The primary diagnosis table stores at least one relation between a nursing diagnosis and at least one patient characteristic, wherein each relation has the same probability measure. The secondary diagnosis table stores at least one relation between a nursing diagnosis and at least one patient characteristic, wherein each relation has a corresponding probability measure. In the data processing system of the present invention the diagnosis table and priority table are preferably implemented in a relational database.

The data processing system of the present invention may also include a display for displaying diagnoses from the potential diagnosis list on the basis of the weighted probability measures. For example, the potential diagnosis list could be sorted on the basis of the weighted probability measures, and a sorted list may be displayed.

In another aspect of the present invention, the data processing system also includes a defining characteristics list which contains relations between patient signs and symptoms and defining characteristics. These defining characteristics and the contained relations may be obtained from standard nursing textbooks. In this embodiment, the matching of assessment data to diagnoses includes matching assessment data with signs and symptoms in the defining characteristics list in order to obtain a list of determined characteristics. The patient characteristics in the diagnosis table then correspond to defining characteristics.

In a preferred embodiment of the present invention, the data processing system includes a workstation which has a local memory, and a host station which has a main memory. The host stations and workstations are interconnected by a network to enable communication therebetween. The main memory includes the diagnosis table, similar to the table described above, and a priority table. The workstation receives assessment data, constructs an assessment data file in its local memory for storing received assessment data, matches received assessment data with patient characteristics in the diagnosis table, and constructs a potential diagnosis list in its local memory for storing the diagnosis and corresponding probability measure of matched relations. A workstation also weights the probability measure of each diagnosis in the potential diagnosis list by the priority measure corresponding to the diagnosis from the priority table. In this embodiment, a workstation copies a diagnosis table and a priority table from the main memory of the host station into its local memory.

In this embodiment, there may also be a plurality of care units, wherein a care unit has a plurality of workstations. In this case, a priority table for each care unit is stored in the main memory of the host station, and the priority table for the care unit which contains the workstation is selected and copied into the local memory of the workstation.

BRIEF DESCRIPTION OF THE DRAWING

The foregoing and other objects, features and advantages of the present invention will be better understood in view of the following detailed description made in conjunction with the accompanying drawing in which:

FIG. 4 is a diagram of a data structure for storing relations between secondary diagnoses, defining characteristics and corresponding probability measures;

FIG. 5 is a diagram of a data structure for storing relations between diagnoses and priority measures;

FIG. 9 is an illustration of an interface display through which assessment data is received by the data processing system;

DETAILED DESCRIPTION

Figure 1:
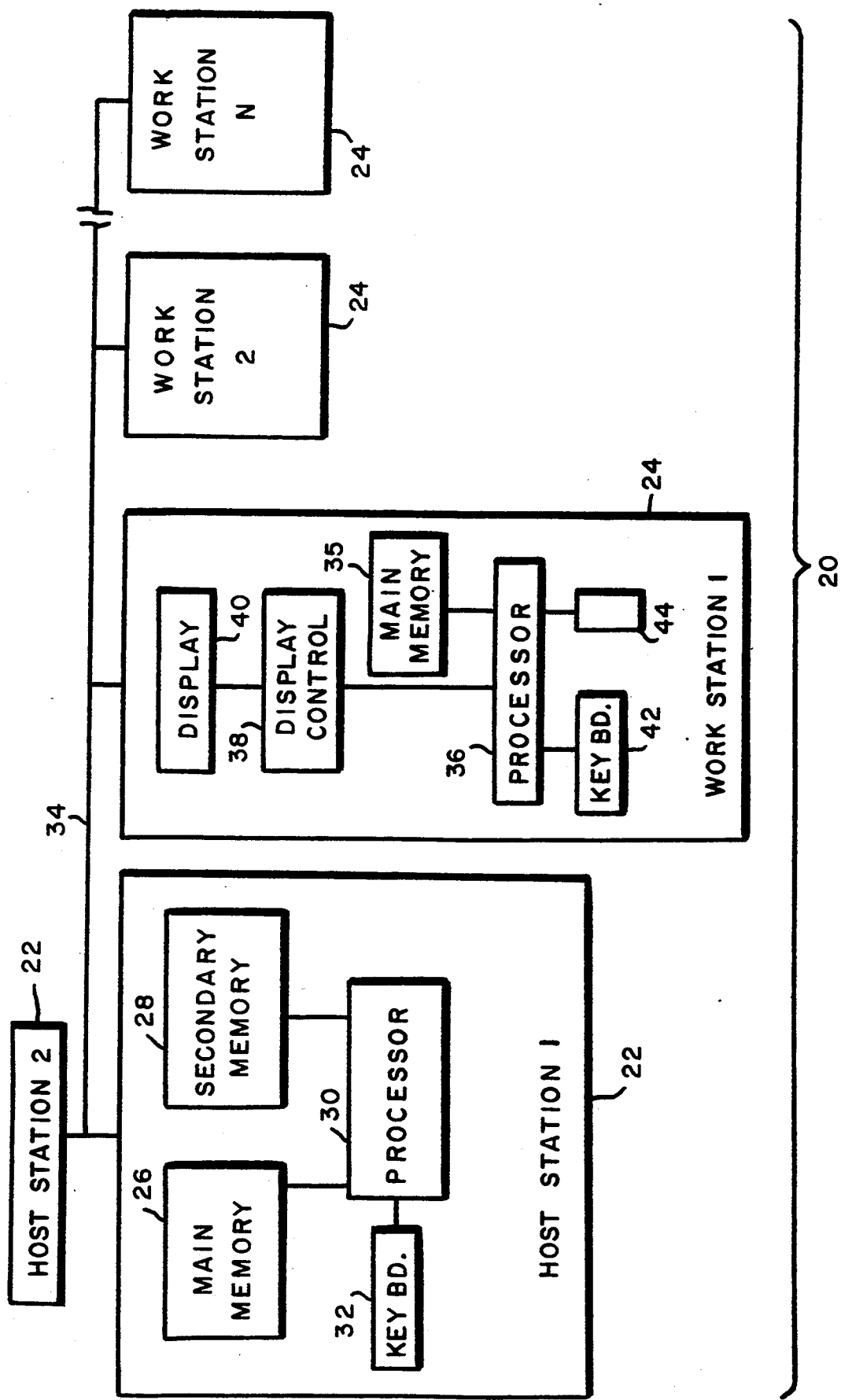
FIG. 1 is a schematic block diagram of a data processing system in which the invention may be employed.

A data processing system 20 in which the present invention may be utilized is illustrated in FIG. 1. The data processing system 20 includes at least one host station 22 and workstations 24. A host station 22 includes a main memory 26 for holding data which may be used by users of the system. A secondary memory 28 is also provided for maintaining the integrity of the database. A processor 30 is provided for reading and writing of data from the data base stored in memory 26, by users at other host stations 22, at workstations 24 and/or at input device 32, such as a keyboard 32, for the host station. It is preferable to have a second host station 22 to provide a redundant data base in case of failure of the first host station. The host stations are, normally and preferably located at a central location within a hospital. Workstations 24, on the other hand, are normally located within a care unit and are connected to the host stations via a network 34.

A workstation 24 normally has a main memory 35 for storing local copies of data and programs and a processor 36 which is capable of performing read and write requests for data from its main memory, and for performing other operations on data. The processor 36 also controls a display control 38 in order to display information on a monitor 40 or other output device. A workstation 24 also includes an input device, such as a keyboard 42 and mouse or trackball 44. Workstations 24, interconnected by network 34, are provided for a care unit, with a workstation 24 preferably being provided for each patient room in a hospital for the preferred embodiment.

Figure 2:
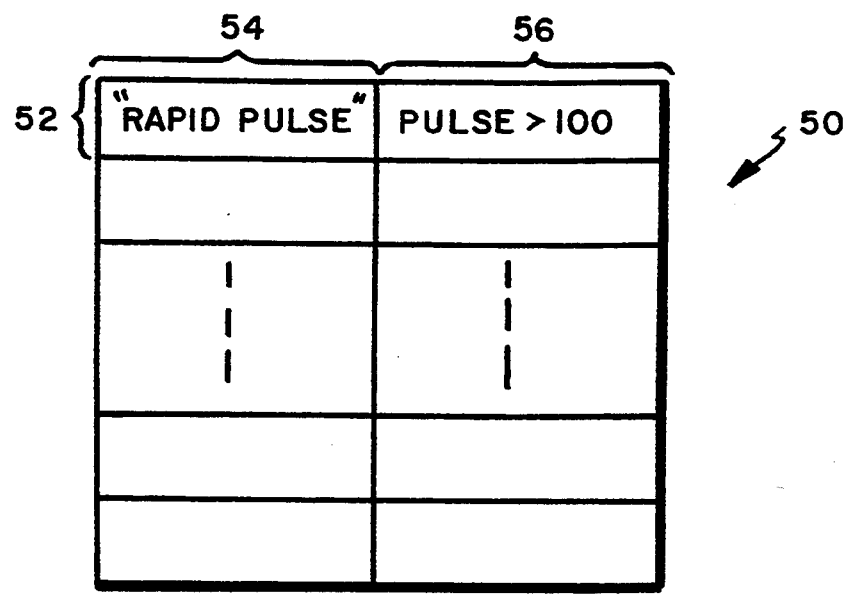
FIG. 2 is a diagram of a data structure for storing relations between defining characteristics and signs and symptoms.

For the preferred embodiment of the present invention, a defining characteristics table is provided, in main memory 26 for identifying the correspondence between possible defining characteristics and patient signs and symptoms (see FIG. 2). The defining characteristics table 50 is a list of entries or relations 52. An entry contains a defining characteristic 54 and at least one corresponding patient symptom 56. The actual correspondence between characteristics 54 and symptoms 56 is well known and used by nurses.

A defining characteristic is matched to or indicated by normally only one patient sign or symptom. However, many signs and symptoms may each individually indicate the same defining characteristic. Thus, a defining characteristic may appear more than once in table 50. However, when diagnoses are made for a patient, a defining characteristic should only be determined once.

Defining characteristics are also related to nursing diagnoses in ways well known to nurses, such as described in *Nursing Diagnosis and Intervention*, by Gertrude K. McFarland and Elizabeth A. McFarlane, (St. Louis: C. V. Mosbe Co., 1989). Such relationships are also embodied in a list in the present invention. According to the preferred embodiment of the present invention, two diagnosis tables are provided.

Figure 3:
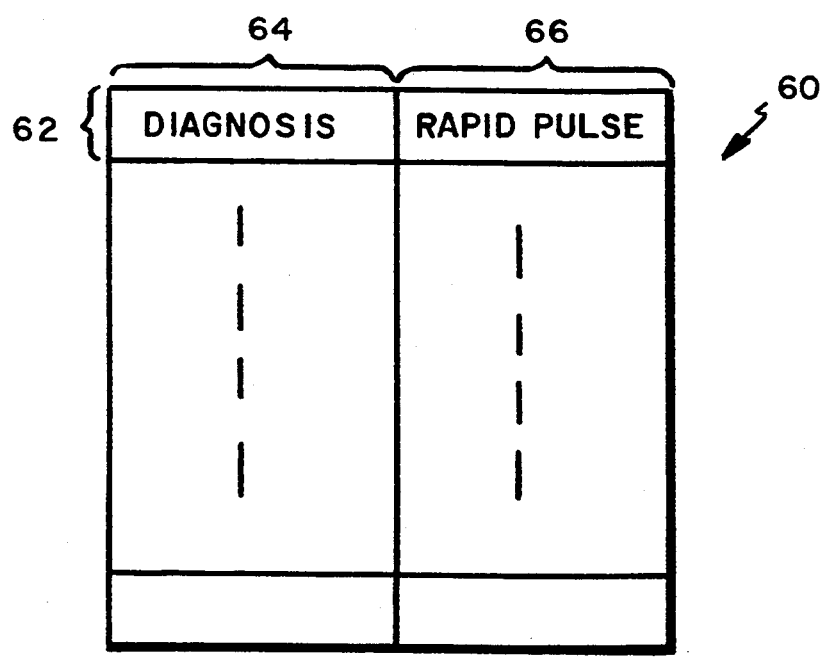
FIG. 3 is a diagram of a data structure for storing relations between primary diagnoses and defining characteristics.

FIG. 3 illustrates a data structure for storing primary diagnoses, called the primary diagnosis list 60. A primary diagnosis list includes entry pairs (or relations) 62, which map defining characteristics to nursing diagnoses. An entry or relation 62 has a diagnosis field 64 for indicating a diagnosis and a defining characteristics field 66 for indicating the defining characteristics corresponding to the diagnosis. All entries or relations in the primary diagnosis list 60 are assumed to have the same probability measure. This list 60 would typically be used for storing diagnostic relations having a probability measure of about 99%. Thus, the values for probability measures for these diagnoses need not be stored nor searched for, saving both time and space.

FIG. 4 is a similar table, called the secondary diagnosis table 70. The secondary diagnosis table 70 has entries or relations 72 similar to entries 62 of the primary diagnosis list 60. However, in addition to the diagnosis field 74 and defining characteristics field 76, there is provided a probability field 78 which indicates the probability measure of the accuracy of the diagnosis indicated by field 74 in an entry 72.

In both the primary diagnosis list 60 and secondary diagnosis list 70, it is possible for a defining characteristic to be related to more than one diagnosis, and for one diagnosis to have more than one corresponding defining characteristic. Thus, when the system is used to perform diagnoses, if multiple results for a single diagnosis are found, they are combined. A suitable combination will be described later in connection with FIGS. 10-14.

After a list of potential diagnoses for a patient is developed, such a list is prioritized, in order to assist the nurse in developing a care plan for the patient. Prioritization may be provided by using a diagnosis priority table 80 (FIG. 5) which includes entries 82 which map diagnoses to priority values. An entry 82 has a diagnosis field 84 and corresponding priority field 86. The value of priority field 86 is intended to be combined with a determined probability for a diagnosis such that a list of diagnoses with combined probability and priority values may obtained. This list is sorted according to the combined values such that the first diagnosis of the sorted list is the diagnosis with the highest probability and priority. A priority measure for a diagnosis is assigned normally according to the importance or severity of the diagnosis within the care unit.

The defining characteristics list 50, primary diagnosis list 60, secondary diagnosis list 70 and priority table 80 are preferably implemented in a relational database. A suitable language, such as DBASE, may be used. To reduce the time for determining valid diagnoses from defining characteristics, it is preferable that entries 52, 62, 72, and 82 be ordered according to the values searched therein. For example, the defining characteristics for a patient are determined and searched for on the basis of symptoms as indicated in field 56 of the defining characteristics list 50. The primary diagnosis table is searched on the basis of the defining characteristics as indicated by field 66. Similarly, secondary diagnosis list 70 is searched on the basis of defining characteristics field 76. Finally, priority table 80 is searched on the basis of diagnosis field 84. By ordering these lists according to the above-identified fields, optimized searching may be realized.

An advantage of using a relational database for the implementation of at least the tables and lists 50, 60, 70, and 80 is the ease with which tools may be provided for modifying these tables and lists, which may be understood as the "rules" of the expert system. Using a relational database a nurse may change the tables and lists without the intervention of a programmer or other skilled computer technician. Thus, when nursing diagnoses, probability measures or priority measures change, a nurse, who is best suited to change the database because of her better understanding of the subject matter, may readily make the changes. A relational database with suitable access tools will enable a nurse to change the database without the intervention of a computer technician.

It is further preferable to provide probability and priority measures which are specific for or dependent on a care unit. For example, by providing multiple priority fields 86, retrievable according to care unit, different care units within a hospital may assign different priorities to different diagnoses. Moreover, similar structures could be used for diagnosis tables 60 and 70 since the probability that a defining characteristic may indicate a certain diagnosis may vary between care units.

When the system of the present invention is used with such care unit-dependent data, a workstation 24 may retrieve data from a host station 22 and need only load information pertaining to the care unit in which the workstation 24 is located. Thus, from the point of view of a care unit, there is only one set of diagnosis data (i.e., diagnosis and priority tables 60, 70 and 80).

It may also be possible to combine the defining characteristics table 50, primary diagnosis list 60 and secondary diagnosis list 70 (FIGS. 2, 3 and 4 respectively) into one table. This table would map signs and symptoms directly to diagnoses and corresponding probabilities. Although such a table may reduce the number of different types of searches on the database, it may cause the database to be larger.

Figure 6:
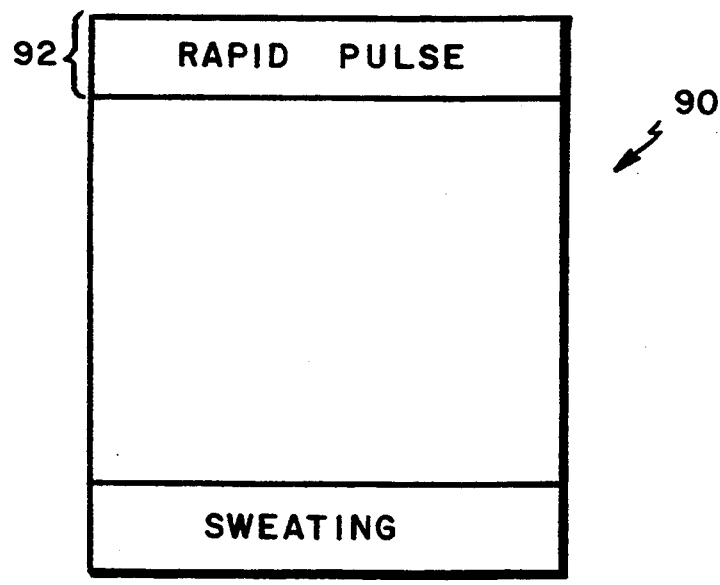
FIG. 6 is a diagram of a data structure for storing patient assessment data or defining characteristics based upon the assessment data.

In the preferred embodiment two temporary data structures are provided for developing a prioritized list of diagnoses for a patient. The first of these data structures is the determined characteristics list 90 (FIG. 6). This list of determined characteristics includes entries 92, the number of which corresponds to the number of defining characteristics retrieved from table 50 which are supported by the assessment data retrieved for a patient. The construction of the determined characteristics list 90 for a patient will be described in further detail below in connection with FIGS. 9–11.

Figure 7:
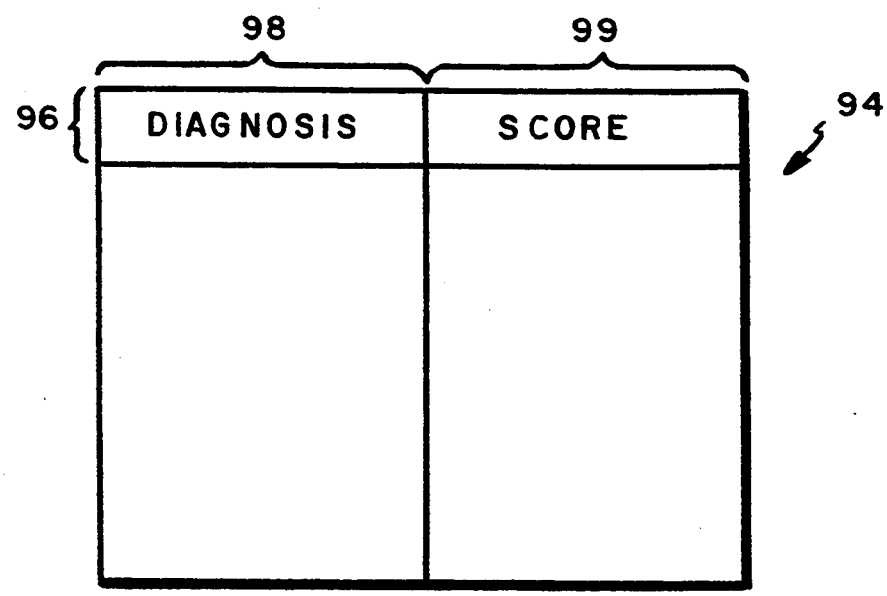
FIG. 7 is a diagram of a data structure for storing determined diagnoses and related combination probabilities and priority measures.

The second of the temporary data structures is the potential diagnosis list 94 (FIG. 7). The potential diagnosis list includes entries 96 which include a diagnosis field 98 for indicating a potential diagnosis, and a score field 99, indicating the probability, possibly prioritized, measure for the corresponding diagnosis. The use of this table will be described in more detail below in connection with FIGS. 12–14.

The process of creating and displaying the list of prioritized diagnoses from patient assessment data will now be described in connection with FIGS. 8–14. The general method of making diagnoses involves steps for retrieving assessment data for a patient and matching it to the defining characteristics database 50. Thus, a list of defining characteristics for the patient is determined. From these determined characteristics, diagnoses may be determined by matching the characteristics to relations in the primary and secondary diagnosis relations lists 60 and 70. If a diagnosis is found more than once, probabilities for the diagnosis are combined. One way to combine the probabilities is by adding them. The list of diagnoses may then be prioritized by combining the probability for a diagnosis with its priority measure found in table 80. The list is then sorted according to score and an ordered, prioritized list may be displayed in a suitable manner to the nurse.

Figure 8:
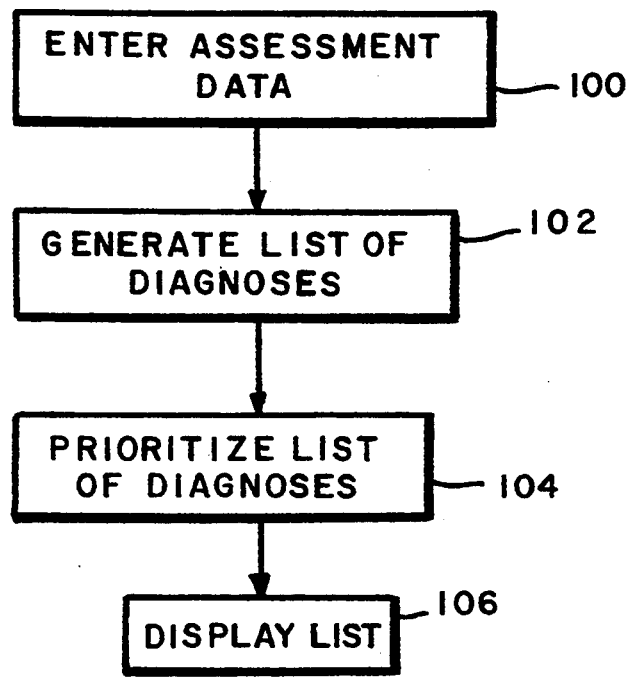
FIG. 8 is a general flowchart of the process for generating and prioritizing diagnoses based on assessment data.
Figure 10:
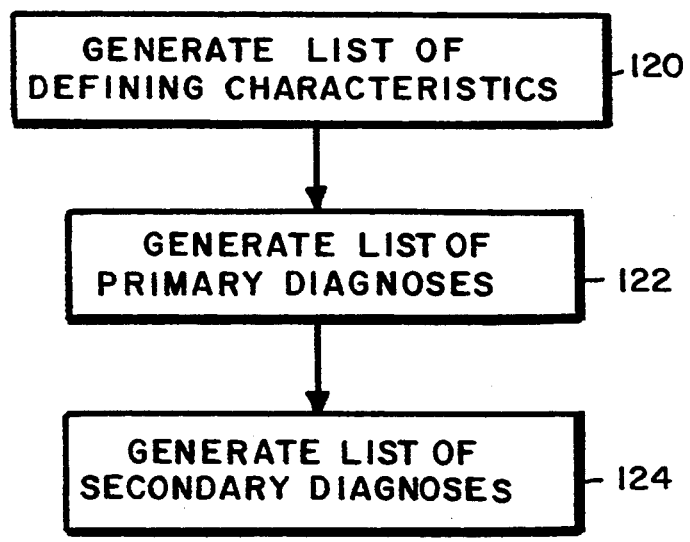
FIG. 10 is a general flowchart of the process for generating diagnoses.

This process is described in general by the flow chart of FIG. 8. The first step of the process is step 100 of entering assessment data for a patient. This process will be described in more detail in connection with FIG. 9. The next step of the process is step 102 of generating a list of diagnoses based on the entered assessment data. Step 102 of generating the list of diagnoses is described in more detail below in connection with FIGS. 10–13. After a list of diagnoses is generated, the diagnosis list is prioritized in step 104. This step 104 of prioritization is described in more detail below in connection with FIG. 14. The process of the present invention concludes with displaying the list of prioritized diagnoses to the nurse on the display 44 of the workstation 24 (FIG. 1) or other output device, in a manner known to those skilled in the art.

Reception of assessment data for a patient will now be described in more detail in connection with FIG. 9. FIG. 9 illustrates a display interface which allows a nurse to enter assessment data for a patient. By providing a standard menu 110 on a display, a nurse may select a "data entry" item (display item 112), which causes entry fields to be displayed. Selection may be performed by, for example, a mouse event, such as a user pointing a cursor on the display item and clicking a button. A list 114 of data entry options, including anatomic systems, is preferably provided from which a nurse may choose to enter data for a patient. In the sample display of FIG. 9, "CV System" (i.e. cardiovascular system) is selected and possible assessment items are displayed in area 116 of the display. A nurse may select an entry item and enter the corresponding data, such as item 117 which is selected to indicate that "peripheral pulses" are abnormal. An interface to receive assessment data may be provided in many ways which are familiar to those skilled in the art of data processing systems. Defining characteristics or corresponding patient systems for which assessment data may be entered are well known to nurses and may be found in standard nursing handbooks.

When a list of patient signs and symptoms has been retrieved, a list of diagnoses may be obtained by the data processing system of the present invention in a manner which will now be described in connection with FIGS. 10–13. In the preferred embodiment of the present invention, the process of generating a list of diagnoses includes step 120 of generating a list of defining characteristics, to be described below in connection with FIG. 11. From the list of defining characteristics, a list of primary diagnoses is then generated in step 122. This process will be described in more detail in connection with FIG. 12. A list of secondary diagnoses is also generated in step 124 from the generated defining characteristics. It is possible to combine these three steps into one step, as shown in step 102 of FIG. 8, when a combined database is provided for the tables 50, 60, and 70 of FIGS. 2, 3, and 4 respectively. That is, one table could be provided for mapping diagnoses directly to lists of patient signs and symptoms, wherein each diagnostic relation has a probability measure field.

Figure 11:
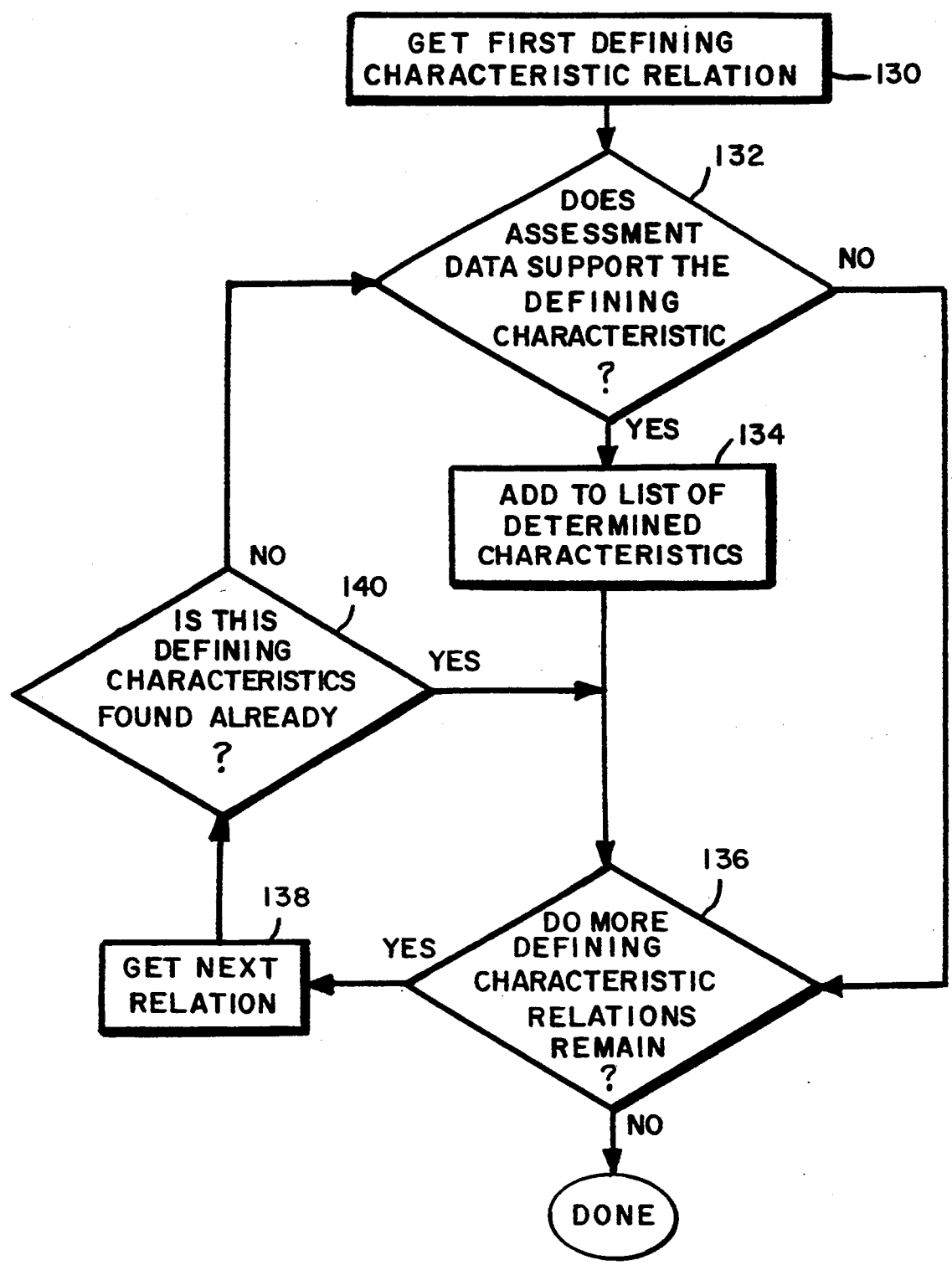
FIG. 11 is a flowchart of the process for determining defining characteristics for a patient from the received assessment data.

The generation of a list of defining characteristics (step 120 of FIG. 10) will now be described in further detail in connection with FIG. 11. Generation of the list of defining characteristics for a patient begins with step 130 of retrieving the first defining characteristic relation 52 from the defining characteristics list 50 (FIG. 3). Next, in step 132, it is determined whether the assessment data from the patient supports the defining characteristic currently examined. Step 132 entails matching the assessment data to the sign or symptom related to the current defining characteristic in field 56. The assessment data is simply searched for the sign or symptom from field 56. If there is a match, the defining characteristic indicated by field 54 is added to the list of determined characteristics 90 (FIG. 6) in step 134. If the assessment data does not match, or, after the defining characteristic is added to the list of determined characteristics, it is determined in step 136 whether more defining characteristic relations (52) remain to be examined. If no relations 52 remain, this process is completed; otherwise, the next relation 52 is retrieved in step 138. The list of determined characteristics 90 is then examined to find if the defining characteristic of this next relation 52 has been found already (step 140). If this defining characteristic has been found, processing continues with step 136 of determining if more relations remain in the defining characteristics list 50. Otherwise, for this next relation 52, processing continues with step 132, as described above. Through the completion of the process described in the flowchart of FIG. 11, a list of determined characteristics 90 may be generated from the assessment delta for a patient.

Figure 12:
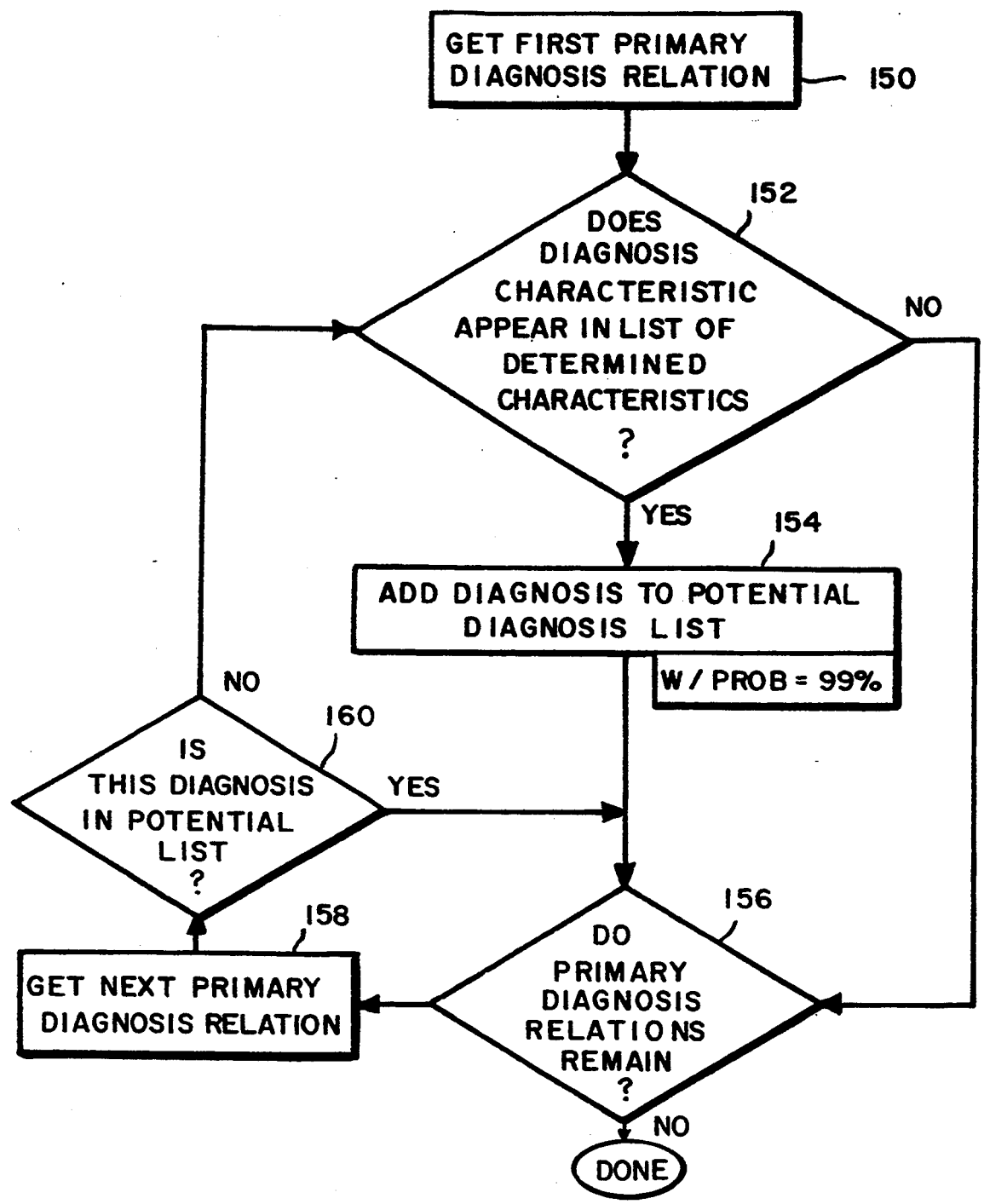
FIG. 12 is a flowchart of the process for determining primary diagnoses and adding them to a potential diagnosis list on the basis of the determined defining characteristics.

The process of generating a list of primary diagnoses (step 122, FIG. 10) will now be described in connection with FIG. 12. The first step of this process is retrieving the first primary diagnosis relation 62 from the primary diagnosis list 60 (FIG. 3) in step 150. Next, it is determined in step 152 if the defining characteristic indicated in field 66 of the currently examined entry 62 appears in the list of determined characteristics 90 described above. If this defining characteristic is in the list of determined characteristics, the diagnosis from field 64 of the currently examined entry 62 is added to the potential diagnosis list 94 as an entry 96, with the diagnosis field 98 set to the currently examined diagnosis, and the score field 99 set to a probability of 99% (step 154).

After a diagnosis is added to the potential diagnosis list during step 154, or it is determined that the defining characteristic field 66 for the diagnosis (field 64 of the currently examined entry 62) does not appear in the list of determined characteristics 90 (determined by step 152), a determination is made during step 156 whether primary diagnosis relations remain in primary diagnosis list 60 to be examined. If an entry 62 remains, the next entry is retrieved in step 158. Next, it is determined in step 160 whether the currently examined diagnosis is already in the potential diagnosis list. Since, in the preferred embodiment, the probability for a potential diagnosis may not exceed 99%, if a diagnosis appears in the potential diagnosis list, further occurrences of it in the primary diagnosis table 60 need not be examined to determine potential diagnoses. After step 160, if the next primary diagnosis is not on the potential diagnosis list, processing continues with step 152 as described above.

The process of generating the list of secondary diagnoses will now be described in connection with FIG. 13. The first step of this process is step 170 of retrieving the first secondary diagnosis relation 72 from the secondary diagnosis table 70. It is then determined in step 172 if the currently examined diagnosis characteristic (field 76) appears in the list of determined characteristics 90 as described above in connection with FIG. 12, step 152. If only one step is used for generating the list of diagnoses (see step 102 of FIG. 8), this step 172 would involve examining the assessment data to determine if it supports the diagnosis of the current relation 92 being examined. If the currently examined relation is supported by the determined characteristics, the list of potential diagnoses 94 is examined to determine if the currently examined diagnosis already exists in the list (step 174). If the currently examined diagnosis does not appear in the list of potential diagnoses 94, it is added to the list of potential diagnoses in step 176. An entry 96 is established with diagnosis field 98 set to the currently examined diagnosis and score field 99 set to the probability as retrieved from the secondary diagnosis table 70, field 78 for that diagnosis. If the currently examined diagnosis does appear on the list of potential diagnoses 94, as determined in step 174, the probability for the currently examined relation 72 (field 78) is added to the existing score (field 99) for the diagnosis in the potential diagnosis list. If the resulting score is greater than 99%, the score is then set to 99% (step 178). After the entry for the currently examined diagnosis is set in the list of potential diagnoses 94, as performed by step 176 or 178, it is determined in step 180 whether secondary diagnoses remain to be examined. If no secondary diagnosis relations remain, this process is complete; otherwise, the next secondary diagnosis relation 72 is retrieved in step 182 and processing continues, as described above, with step 172.

Figure 13:
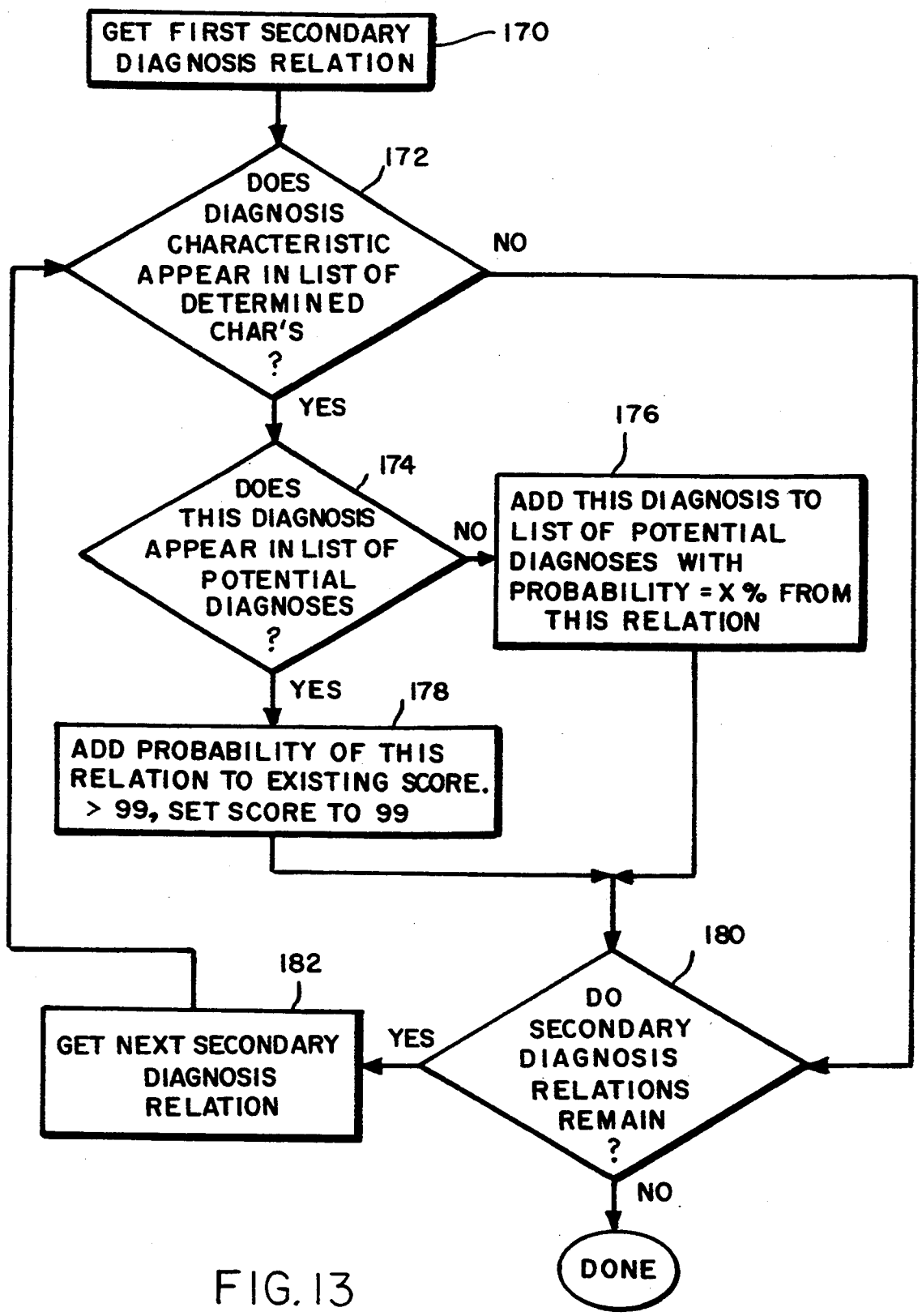
FIG. 13 is a flowchart of a process for determining secondary diagnoses and adding them to the list of potential diagnoses on the basis of the determined defining characteristics.
Figure 14:
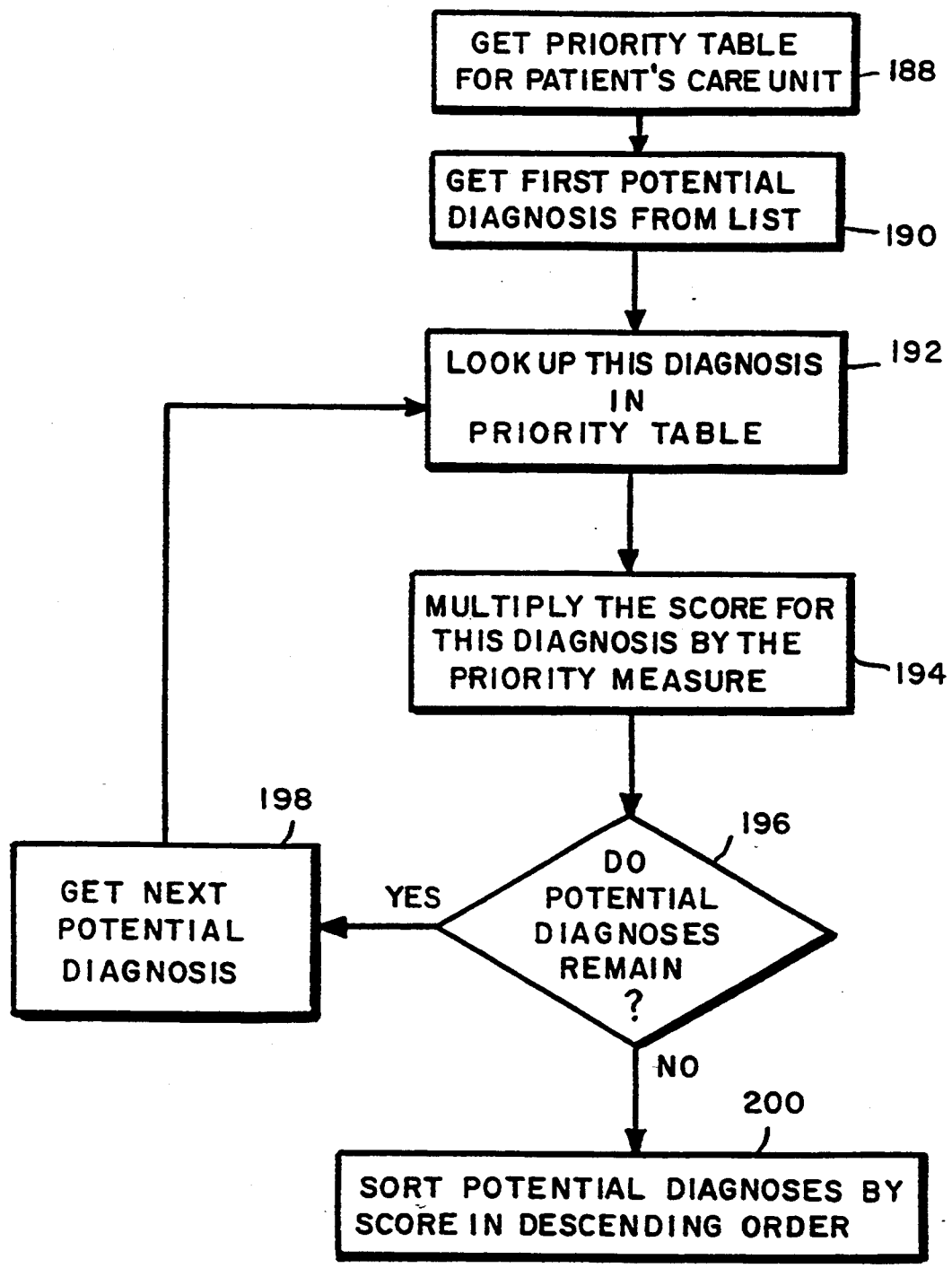
FIG. 14 is a flowchart of a process for prioritizing determined diagnoses.

By the completion of the process illustrated by the flowchart of FIG. 13, a list of potential diagnoses 94 is generated for a patient, wherein each diagnoses appear once, and each diagnosis has a score representing its probability, with a highest probability of 99%. This list of potential diagnosis is prioritized and sorted in a manner which will now be described in connection with FIG. 14.

The first step of the preferred method of prioritization is step 188 of getting the priority table for the patient's care unit, followed by step 190 of retrieving the first potential diagnosis from the list 94. The priority value for this diagnosis is retrieved from the priority table 80 by searching for an entry 82 having the corresponding diagnosis in field 84, in step 192. The priority value retrieved from field 86 is then multiplied with the score for the diagnosis, in step 194, which is retrieved from field 99 of the entry 96 for the diagnosis in the potential diagnosis list 94. It is then determined in step 196 whether potential diagnoses in the list 94 remain to be examined. If potential diagnoses remain, the next diagnosis is retrieved from the list 94 in step 198 and processing continues with step 192 as described above. Otherwise, if all potential diagnoses have been examined, the potential diagnosis list is sorted by score in descending order (step 200). Thus, the diagnosis having the largest product of priority measure and probability will appears first in the list. The prioritized list may be stored, if desired, in the database along with other patient information.

The sorted potential diagnosis list may then be displayed in a suitable manner to the nurse using the system (step 202), in order to provide a list of prioritized diagnoses to the nurse. If desired, the scores corresponding to the diagnoses may also be displayed to give the nurse an indication of the relative priority of the determined diagnoses.

Having now described an embodiment of the invention it should be apparent to those skilled in the art that the foregoing description is illustrative only and not limiting, having been presented by way of example only. Numerous other embodiments and modifications thereof are contemplated as falling within the scope of the present invention as defined by the appended claims and equivalents thereto.

What is claimed is:

1. A computer system for generating a prioritized list of possible nursing diagnoses from assessment data, comprising:

a memory for storing a first plurality of relations between nursing diagnoses and patient characteristics, each relation having a corresponding probability measure;

a memory for storing a a second plurality of relations between nursing diagnoses and priority measures;

data entry and data display means in the computer system for receiving assessment data from nursing personnel;

computer control means for matching received assessment data with patient characteristics in the first plurality of relations;

computer control means for constructing a potential diagnosis list containing the diagnosis and corresponding probability measure of each relation of the first plurality containing a matched patient characteristic;

computer control means for weighting each probability measure in the potential diagnosis list by the priority measure of its corresponding diagnosis from the priority table; and a memory for storing the potential diagnosis list as a list of possible nursing diagnoses prioritized according to the weighted probability measures.

2. A computer system as set forth in claim 1 wherein the first plurality of relations includes more than one relation for at least one nursing diagnosis; and wherein said computer control means for constructing a potential diagnosis list includes means for combining probability measures related to a diagnosis having more than one relation, said diagnosis having more than one relation appearing once in the potential diagnosis list with a corresponding probability measure substantially equal to the combined probability measure.

3. A computer system as set forth in claim 2 wherein the means for combining probability measures includes means for adding said probability measures together.

4. A computer system as set forth in claim 3 wherein the maximum combined probability measure for a diagnosis in the potential diagnosis list is equivalent to 99%.

5. A computer system as set forth in claim 4 further comprising means for displaying diagnoses from the potential diagnosis list on the basis of the weighted probability measures.

6. A computer system as set forth in claim 1 wherein the memory for storing a first plurality of relations stores a primary diagnosis table and a secondary diagnosis table, said primary diagnosis table containing at least one relation between a nursing diagnosis and at least one patient characteristic, each relation having the same probability measure, and said secondary diagnosis table containing at least one relation between a nursing diagnosis and at least one patient characteristic, each relation having a corresponding probability measure.

7. A computer system as set forth in claim 6, further comprising means for storing a defining characteristics list containing relations between signs and symptoms and defining characteristics, and wherein said computer control means for matching includes means for matching assessment data with signs and symptoms in the defining characteristics list to obtain a list of determined characteristics, and wherein said patient characteristics in said first plurality of relations are defining characteristics.

8. A computer system as set forth in claim 7, wherein said first and second pluralities of relations are implemented in a relational database.

9. A computer system for determining prioritized nursing diagnoses for a patient from assessment data, said system comprising:
at least one workstation having a local memory;
at least one host station having a main memory;
a network interconnecting said host station and workstation for enabling communication therebetween;
said main memory containing a diagnosis table for storing at least one relation between a nursing diagnosis and a patient characteristic, each relation having a corresponding probability measure, and a priority table for storing at least one relation between a nursing diagnosis from the diagnosis table and a corresponding priority measure; and
wherein said workstation includes means for receiving assessment data, means for constructing an assessment data file in its local memory for storing the received assessment data, means for matching received assessment data with patient characteristics from relations in the diagnosis table, means for constructing a potential diagnosis list in its local memory for storing the diagnosis and corresponding probability measure of matched relations; and means for weighting each probability measure in the potential diagnosis list by the priority measure of its corresponding diagnosis from the priority table.

10. A computer system as set forth in claim 9, wherein each of said workstations further includes means for copying said diagnosis table and said priority table from the main memory of the host station into its local memory.

11. A computer system as set forth in claim 10, wherein there are a plurality of care units, there being a plurality of said workstations for at least one care unit, wherein there is a respective priority table stored in the main memory of the host station for each care unit; and
wherein said means for copying said priority table into the local memory of a workstation includes means for selecting and copying the priority table for the care unit containing the workstation.

12. A method for determining prioritized nursing diagnoses from assessment data using computer system having memory and control means, comprising the computer-implemented steps of:
storing in the memory a diagnosis table containing a plurality of relation between nursing diagnoses and patient characteristics, each relation having a corresponding probability measure;
storing in the memory a priority table containing a plurality of relations between nursing diagnoses and priority measures;
the control means creating a computer-readable form of assessment data;
the control means matching assessment data with relations in the diagnosis table;
the control means constructing a potential diagnosis list containing the diagnosis and corresponding probability measure of each matched relation;
the control means weighting each probability measure in the potential diagnosis list by the priority measure of its corresponding diagnosis from the priority table; and
storing in the memory the potential diagnosis list as a list of possible nursing diagnoses prioritized according to the weighted probability measures.

13. A method as set forth in claim 12 wherein the diagnosis table includes more than one relation for at least one nursing diagnosis; and
wherein said step of constructing a potential diagnosis list includes the step of combining probability measures related to a diagnosis having more than one relation, said diagnosis having more than one relation appearing once in the potential diagnosis list with a corresponding probability measure equal to the combined probability measures.

14. A method as set forth in claim 13 wherein the step of combining probability measures includes the step of adding said probability measures together.

15. A method as set forth in claim 14 wherein the maximum combined probability measure for a diagnosis in the potential diagnosis list is equivalent to 99%.

16. A method as set forth in claim 15 further comprising the step of displaying diagnoses from the potential diagnosis list on the basis of the weighted probability measures.

17. A method as set forth in claim 12 wherein the diagnosis table includes a primary diagnosis table and a secondary diagnosis table, said primary diagnosis table containing at least one relation between a nursing diagnosis and at least one patient characteristic, each relation having the same probability measure, and said secondary diagnosis table for storing at least one relation between a nursing diagnosis and at least one patient characteristic, each relation having a corresponding probability measure.

18. A method as set forth in claim 17, further comprising the step of providing a defining characteristics list containing at least one relation between signs and symptoms and defining characteristics, and wherein said step of matching includes the step of matching assessment data with signs and symptoms in the defining characteristics list to obtain a list of determined characteristics, and wherein said patient characteristics in said first plurality of relations are defining characteristics.

* * * * *